(12) United States Patent
Ma et al.

(10) Patent No.: US 11,994,419 B2
(45) Date of Patent: May 28, 2024

(54) APPARATUS FOR MONITORING OF THE MULTIPHASE FLOW IN A PIPE

(71) Applicant: ENERCORP ENGINEERED SOLUTIONS, LLC, New Castle, DE (US)

(72) Inventors: Lu Ma, Basingstoke (GB); Yessica Arellano, Basingstoke (GB)

(73) Assignee: ENERCORP ENGINEERED SOLUTIONS INC., Calgary (CA)

( * ) Notice: Subject to any disclaimer, the term of this patent is extended or adjusted under 35 U.S.C. 154(b) by 157 days.

(21) Appl. No.: 17/255,306

(22) PCT Filed: Jun. 28, 2019

(86) PCT No.: PCT/EP2019/067427
§ 371 (c)(1),
(2) Date: Dec. 22, 2020

(87) PCT Pub. No.: WO2020/002649
PCT Pub. Date: Jan. 2, 2020

(65) Prior Publication Data
US 2021/0270645 A1  Sep. 2, 2021

(30) Foreign Application Priority Data
Jun. 29, 2018 (GB) .................................... 1810735

(51) Int. Cl.
*G01F 1/58* (2006.01)
*G01F 1/74* (2006.01)

(52) U.S. Cl.
CPC ............... *G01F 1/586* (2013.01); *G01F 1/74* (2013.01)

(58) Field of Classification Search
CPC ... G01F 1/586; G01F 1/74; G01F 1/58; G01F 1/582; G01F 1/712; G01V 3/08;
(Continued)

(56) References Cited

U.S. PATENT DOCUMENTS 5,789,830 A * 8/1998 Portegies ........... H02K 41/0356
                                                    310/12.33
9,631,750 B1 * 4/2017 Veazey ................. F16L 23/003
(Continued)

FOREIGN PATENT DOCUMENTS

CN   101871906 A   10/2010
CN   104864921 A   8/2015
(Continued)

OTHER PUBLICATIONS

GB Search and Examination Report for GB Application No. GB1810735.9, entitled "Apparatus For Monitoring Of The Multiphase Flow In A Pipe," dated Nov. 1, 2018.
(Continued)

*Primary Examiner* — Peter J Macchiarolo
*Assistant Examiner* — John M Royston
(74) *Attorney, Agent, or Firm* — MH2 TECHNOLOGY LAW GROUP LLP (57) ABSTRACT

A monitoring apparatus for monitoring a multiphase flow in a pipe using magnetic induction tomography, the apparatus comprising a tubular member adapted for fitting around a pipe defining a flow conduit, wherein the tubular member has outer and inner tubular surfaces surrounding a central longitudinal axis of the tubular member, the inner tubular surface defining a central bore extending along the central longitudinal axis for receiving a pipe therealong, wherein the outer tubular surface has a polygonal cross-section and is comprised of an annular array of a plurality of planar faces, each planar face extending parallel to the central longitudinal axis, wherein at least two of the planar faces each includes a respective coil mounting portion on which is mounted a respective electrical coil, wherein the coil mounting portion comprises a recess in the tubular outer surface which receives a respective electrical coil.

23 Claims, 5 Drawing Sheets

(58) Field of Classification Search
CPC .... G01V 3/10; G01N 33/2823; G01N 27/025; G01N 27/07; G01N 27/08; G01P 5/001; G01P 5/08; G01P 5/22
See application file for complete search history.

(56) References Cited

U.S. PATENT DOCUMENTS

| | | | |
|---|---|---|---|
| 10,378,941 B2 | 8/2019 | McCann | |
| 10,739,177 B2 | 8/2020 | McCann | |
| 10,753,778 B2 | 8/2020 | McCann | |
| 2009/0025486 A1 | 1/2009 | Cros et al. | |
| 2018/0067590 A1* | 3/2018 | Wang | G06F 3/046 |
| 2018/0284157 A1* | 10/2018 | Inoue | G01R 11/24 |

FOREIGN PATENT DOCUMENTS

| | | |
|---|---|---|
| GB | 2 424 955 A | 11/2006 |
| GB | 2 507 368 B | 4/2014 |
| GB | 2 513 678 B | 11/2014 |
| GB | 2 513 679 B | 11/2014 |
| GB | 2 527 324 B | 12/2015 |
| GB | 2 534 337 B | 7/2016 |
| GB | 2 530 601 B | 10/2017 |
| JP | H01178822 A | 7/1989 |

OTHER PUBLICATIONS

PCT International Search Report and Written Opinion for International Application No. PCT/EP2019/067427, entitled "Apparatus For Monitoring Of The Multiphase Flow In A Pipe," dated Sep. 26, 2019.

Peyton et al., "Development of Electromagnetic Tomography (EMT) for Industrial Applications. Part 1: Sensor Design and Instrumentation," 1st World Congress on Industrial Process Tomography, Buxton, Greater Manchester, Apr. 14-17, 1999, pp. 306-312.

* cited by examiner

APPARATUS FOR MONITORING OF THE MULTIPHASE FLOW IN A PIPE

This application is the U.S. National Stage of International Application No. PCT/EP2019/067427, filed Jun. 28, 2019, which designates the U.S., published in English, and claims priority under 35 U.S.C. § 119 or 365(c) to United Kingdom Application No. 1810735.9, filed Jun. 29, 2018. The entire teachings of the above applications are incorporated herein by reference.

The present invention relates to a monitoring apparatus for monitoring a multiphase flow in a pipe using magnetic induction tomography. The multiphase flow comprises fluids, and may comprise a mixture of liquids, or one or more liquids in a mixture with solids and/or gases. This invention particularly relates to a multiphase flow metering apparatus which has a number of applications, in particular within the oil and gas exploration and production industry.

A number of prior patent specifications in the name of the Applicant are directed to the use of Magnetic Induction Tomography (MIT), either used alone or in conjunction with other techniques, for monitoring a multiphase flow in a pipe, in particular in the oil and gas exploration and production industry.

In particular, GB2513678B discloses an "Oil well system and operating method including monitoring multiphase flow in a pipe", GB2513679B discloses a "Method of defining a multiphase flow comprising three phases", GB2507368B discloses "Method and apparatus for monitoring the flow of mixtures of fluids in a pipe", GB2534337B discloses "Method and apparatus for monitoring of the multiphase flow in a pipe" and GB253060113 discloses "Method and apparatus for monitoring of the multiphase flow in a pipe".

In these prior specifications, helical and circular transmitting and receiving coils are located around the outside of a pipe. In this specification, the term "helical" means a non-planar spiral in three dimensions, i.e. having the shape of a geometrical helix. The transmitting coil(s) are supplied with a varying current which transmits electromagnetic field into a multiphase flow within the pipe. The electromagnetic field induces eddy currents in a conductive phase within the pipe resulting in a secondary electromagnetic field. The secondary electromagnetic field induces an electric field which can be measured in the receiving coil(s) via voltage output that can be analysed to determine properties of the multiphase flow.

In addition, GB2527324B discloses a "Segmented Electromagnetic Sensor".

It is disclosed in these specifications that electromagnetic energy can provide information related to certain physical properties of materials in the multiphase flow exposed to this type of energy. When used in an electromagnetic flowmeter, electrical capacitance tomography (ECT), electrical resistance tomography (ERT) and magnetic inductance tomography (MIT) can be used to interrogate the multiphase flow. In each case a varying electric or magnetic field can be applied across the multiphase flow, and measurements of voltage, current and magnetic field can be used to measure certain physical parameters of the constituent components of the multiphase flow.

Apart from these prior patent specifications and other disclosure by the present Applicant or its employees or the present inventors, although MIT is known for use in various medical applications, the present inventors are not aware of any other disclosure in the context of providing real time data on oil/gas/water multiphase flow imaging, for example for use in the oil and gas industry. It is known from such medical applications to use various coil geometry developments for static or semi-static fluid tests using helical coils with various numbers of turns. However, no optimum coil performance for flow measurement has been defined.

Known MIT systems use circular helical coils for static, or quasi-static, fluid measurement. Furthermore, known MIT systems use separate bodies for the coil mount/former, the electromagnetic shield structure and the fluid container. In traditional MIT systems, the coils are wound around formers which restricts the operational flexibility when there is a need to replace the coils.

In the prior art, there two main approaches for coil positioning around a cylindrical fluid container. One approach consists of attaching the coil formers to a shield structure. The other approach fixes cylindrical coil formers to the fluid container.

Although previous solutions comply with MIT requirements in terms of sensor arrangements being equally spaced and symmetrically positioned around the region of interest (ROI), these known assemblies need to be improved to provide greater flexibility in construction and operation.

Although the patent specifications identified above disclose a monitoring apparatus for monitoring a multiphase flow in a pipe using magnetic induction tomography which can effectively monitor such a multiphase flow, there is nevertheless a need in the art for an improved monitoring apparatus.

In particular, there is a need in the art for a monitoring apparatus which has an enhanced flexibility as compared to known MIT apparatus for monitoring multiphase flows in a pipe.

There is a further need in the art for a monitoring apparatus which can be used reliably, efficiently and flexibly to install transmitter/receiver coils accurately in position around a pipe.

There is a further need in the art for a monitoring apparatus which can be used accurately to install transmitter/receiver coils equidistantly and symmetrically around a pipe.

There is a further need in the art for a monitoring apparatus which can be used reliably, efficiently and flexibly to avoid or minimise capacitive coupling of transmitter/receiver coils with an external source of electromagnetic radiation and/or to avoid or minimise direct capacitive coupling of the transmitter/receiver coils.

There is a further need in the art for a monitoring apparatus which can be used accurately to distinguish between an electrically conductive phase such as an aqueous phase, for example water, and an electrically non-conductive phase, such as an oil phase, in a multiphase flow, yet is highly flexible in use, and can be fitted to a variety of different pipes in a variety of different locations and orientations using a variety of different coil configurations.

The present invention aims, at least partially, to meet one or more of these needs in the art, particularly in the field of oil and gas exploration and production, to provide enhanced analytical data in real-time on the phase composition of multiphase fluid/solid flows particularly within a pipeline used in the oil and gas industry.

In one aspect the present invention provides a monitoring apparatus for monitoring a multiphase flow in a pipe using magnetic induction tomography, the apparatus comprising a tubular member adapted for fitting around a pipe defining a flow conduit, wherein the tubular member has outer and inner tubular surfaces surrounding a central longitudinal axis of the tubular member, the inner tubular surface defining a central bore extending along the central longitudinal axis for receiving a pipe therealong, wherein the outer tubular surface has a polygonal cross-section and is comprised of an annular array of a plurality of planar faces, each planar face extending parallel to the central longitudinal axis, wherein at least two of the planar faces each includes a respective coil mounting portion on which is mounted a respective electrical coil, wherein the coil mounting portion comprises a recess in the tubular outer surface which receives a respective electrical coil.

In some preferred embodiments the at least two planar faces are each orthogonal to a respective radius of the tubular member.

In some preferred embodiments, each coil mounting portion mounts a respective electrical coil thereon in an orientation such that a central axis of the electrical coil is aligned with a radius of the tubular member.

In some preferred embodiments, the annular array of planar faces comprises n even number of planar faces, the even number being within the range of from 4 to 12, optionally 8, and each planar face includes a respective coil mounting portion on which a respective electrical coil is mounted in a respective recess.

In some preferred embodiments, the inner tubular surface is cylindrical.

In some preferred embodiments, the monitoring apparatus further comprises an inner sleeve member removably fitted within the inner tubular surface to reduce the internal diameter of the central bore.

In some preferred embodiments, the tubular member comprises a plurality of part-tubular portions and at least one attachment mechanism for attaching together the plurality of part-tubular portions to form the tubular member.

Typically, the tubular member comprises first and second semi-cylindrical portions and at least one attachment mechanism for attaching together the first and second semi-cylindrical portions to form the tubular member. The attachment mechanism may preferably function to clamp the tubular member on to the pipe.

For example, the tubular member may comprise first and second attachment mechanisms on opposite longitudinal sides of the tubular member or an attachment mechanism on one longitudinal side of the tubular member and a hinge mechanism on an opposite longitudinal side of the tubular member, the hinge mechanism hingedly connecting the first and second semi-cylindrical tubular portions by a hinge extending parallel to the central longitudinal axis.

Optionally, the attachment mechanism comprises a pair of longitudinal flange members, each flange member being affixed to, or integral with, a respective one of the part-tubular portions, and a fixing device for fixing together the pair of longitudinal flange members. Preferably, the longitudinal flange members include at least one fixing hole extending therethrough and the fixing device comprises at least one bolt mechanism for passage through aligned fixing holes of the longitudinal flange members to attach together the longitudinal flange members. The attachment mechanism preferably further comprises at least one elongate mounting element to which the pair of longitudinal flange members are fitted by the fixing device. The elongate mounting element is preferably adapted to define a plurality of indexed mounting positions therealong, whereby the pair of longitudinal flange members may be fitted to the elongate mounting element at a desired indexed mounting position therealong. Typically, the plurality of indexed mounting positions is defined by a plurality of mounting holes serially arranged along the elongate mounting element.

In some preferred embodiments, the tubular member further a pair of annular flanges, each annular flange being affixed to, or integral with, a respective longitudinal end of the tubular member and wherein at least one annular flange of the pair of annular flanges includes a ring of fitting holes for fitting the respective annular flange to another corresponding annular flange including a respective ring of fitting holes thereby serially to connect together adjacent tubular members in a direction extending along the central longitudinal axis.

Typically, the recess has a planar lower surface and is polygonal in plan. Optionally, the recess is defined between outer and inner peripheral edges which are raised above the respective planar face. In one preferred embodiment, the recess is composed of four linear sections and is rectangular in plan, optionally square in plan.

Typically, the electrical coil comprises an electrically conductive wire which is wound about a central axis to form a plurality of wire turns, wherein each turn is in a common plane so that the respective electrical coil is planar and each turn is composed of a plurality of linear sections and the respective electrical coil is polygonal in plan, and the planar electrical coil is aligned with the respective planar face including the respective coil mounting portion.

In some preferred embodiments, the monitoring apparatus further comprises at least one coil fixing mechanism for fixing an electrical coil to a respective coil mounting portion, wherein the coil fixing mechanism comprises a slidable plate which is slidably attached to the coil mounting portion and is arranged to sandwich the electrical coil between the slidable plate and the respective planar face.

In some preferred embodiments, the coil mounting portion of the respective planar face of the tubular member, or the tubular member, is composed of an electrically non-conductive material.

In some preferred embodiments, the monitoring apparatus further comprises a tubular shield member adapted to be fitted around the tubular member, the shield member being composed of an electrically conductive material to shield against electromagnetic radiation. A cylindrical wall of the shield member may be provided with at least one array of holes extending therethrough for passage therethrough of wires connected to respective coils mounted on respective coil mounting portions.

Typically, the shield member has at least one longitudinal flange which is adapted to be clamped to a longitudinal edge of the tubular member. Additionally or alternatively, the shield member has a hinge extending long a first longitudinal edge of the shield member and, at an opposite second longitudinal edge of the shield member, a pair of overlapping flange portions which are adapted to be fitted together to close the shield member in a tubular configuration, optionally wherein a gasket composed of an electromagnetic interference material is disposed between the pair of overlapping flange portions.

In a second aspect the present invention provides a monitoring apparatus for monitoring a multiphase flow in a pipe using magnetic induction tomography, the apparatus comprising a tubular member adapted for fitting around a pipe defining a flow conduit, wherein the tubular member comprises first and second semi-cylindrical portions and at least one attachment mechanism for attaching together the first and second semi-cylindrical portions to form the tubular member, wherein the tubular member has outer and inner tubular surfaces surrounding a central longitudinal axis of the tubular member, the inner tubular surface defining a central bore extending along the central longitudinal axis for receiving a pipe therealong, wherein the outer tubular surface has a polygonal cross-section and is comprised of an annular array of a plurality of planar faces, each planar face extending parallel to the central longitudinal axis, wherein at least two of the planar faces each includes a respective coil mounting portion on which is mounted a respective electrical coil.

In a third aspect the present invention provides a monitoring apparatus for monitoring a multiphase flow in a pipe using magnetic induction tomography, the apparatus comprising a tubular member adapted for fitting around a pipe defining a flow conduit, wherein the tubular member has outer and inner tubular surfaces surrounding a central longitudinal axis of the tubular member, the inner tubular surface defining a central bore extending along the central longitudinal axis for receiving a pipe therealong, wherein the outer tubular surface has a polygonal cross-section and is comprised of an annular array of a plurality of planar faces, each planar face extending parallel to the central longitudinal axis, wherein at least two of the planar faces each includes a respective coil mounting portion on which is mounted a respective electrical coil, the apparatus further comprising a tubular shield member fitted around the tubular member, the shield member being composed of an electrically conductive material to shield against electromagnetic radiation, wherein the shield member has a hinge extending along a first longitudinal edge of the shield member and, at an opposite second longitudinal edge of the shield member, a pair of overlapping flange portions which are fitted together to close the shield member in a tubular configuration.

The present invention relates specifically to an improved apparatus for the use of MIT (Magnetic Induction. Tomography), in particular in the application of MIT to measuring multiphase flows in the oil and gas and other industries. The principle of MIT is that electric coils are excited with alternating current that results in the coils producing varying electromagnetic fields. The object of interest is placed within these fields and the varying field induces varying currents within the object that is dependent on the conductivity of the object. The varying currents in the object produce secondary electromagnetic fields that can be received by the same or other coils. The received secondary electromagnetic field in conjunction with the primary imposed electromagnetic field can use be used to compute the conductivity contrast between the object and the material that surrounds it.

The preferred embodiments of this invention relate to an apparatus to measure the flow of mixtures of fluids from a well or group of wells during oil and gas exploration, production or transportation operations. However, it should be understood that the apparatus and method of the present invention may be used in other potential applications, as those skilled in the art will appreciate. For example, the apparatus and method of the present invention may be used in flow measurement devices, medical MIT Systems involving measurement of low conductivity contrasts of multiphase fluid flows, and multiphase process monitoring equipment.

The preferred embodiment of the present invention can provide a monitoring apparatus which is configured to install MIT sensors, the form of transmitter/receiver coils for transmitting and/or receiving electromagnetic radiation, equidistantly and symmetrically around the outside of a pipe. Furthermore, the configuration of the transmitter/receiver coils can avoid or minimise capacitive coupling of the coils with an external source of electromagnetic radiation, and can avoid or minimise direct capacitive coupling among the coils.

The preferred embodiments of the present invention can provide a comprehensive design which incorporates a coil mount assembly with a tubular clamp-on mechanism for removably attaching the assembly to a pipe at any desired location along the pipe. The pipe may also be at any desired orientation, for example horizontal, vertical, or at any inclination therebetween.

The coil mount assembly may be provided with one or more removable, and exchangeable, inner pieces to accommodate fitting to varying pipe diameters. The tubular clamp-on mechanism may be adapted to provide variable axial distances between plural planes of coils. The assembly also provides radial electromagnetic shielding around the coil mount assembly.

The preferred embodiments of the present invention can also provide a tubular clamp-on mechanism which provides ease of installation and portability, while ensuring that the electrical coils of the coil mount assembly remain aligned and symmetrically spaced.

The preferred embodiments of the present invention can also provide a tubular clamp-on mechanism which can be customised to have a desired internal cylindrical shape for fitting to a pipeline having a given external diameter. The preferred embodiments of the present invention can also provide a tubular clamp-on mechanism which has an outer polygonal geometry that ensures orthogonality of the coils to a radial direction of the pipe around which the tubular clamp-on mechanism is fitted in operation.

The preferred embodiments of the present invention can also provide coil mounts or formers which allow coils to be readily installed or interchanged without compromising the system integrity.

The preferred embodiments of the present invention can provide a monitoring apparatus having enhanced characteristics as compared to previous solutions. For example, the monitoring apparatus of the preferred embodiments can install the sensors equidistantly and symmetrically around a cylindrical geometry while providing enhanced flexibility in terms of manufacturing, installation, maintenance, and redesign. Additionally, the monitoring apparatus of the preferred embodiments of the present invention combines for the first time a coil attaching mechanism and a shield mounting.

The preferred embodiments of the present invention can provide a monitoring apparatus which can integrate the coil mounts or formers into a tubular clamp-on mechanism that is adapted to be attached externally to a pipe. The monitoring apparatus can provides any or all of: ease of installation of the monitoring apparatus onto or around a pipe or pipeline; a portable and lightweight monitoring apparatus; fixation of coil sensors equidistantly from each other; a variable and precise distance between MIT planes; ease of coil installation on the tubular clamp-on mechanism, and replacement of the coils as required; and adaptability of the monitoring apparatus to varying, in particular smaller, pipe geometries.

The preferred embodiments of the present invention can also provide a shield which ensures there is substantially no radial magnetic leakage between the shield enclosure and the outside environment.

The preferred embodiments of the present invention can provide a monitoring apparatus which incorporates electromagnetic shielding to minimise unwanted capacitive coupling and avoid electromagnetic leakage to the external environment.

The preferred embodiments of the present invention can provide a monitoring apparatus incorporating a tubular split sleeve having a clamp-on configuration containing coil formers for MIT measurement of multiphase flows in a pipe, the a tubular split sleeve being configured to provide a support for a dismountable electromagnetic shield.

Embodiments of the present invention will now be described, by way of example only, with reference to the accompanying drawings, in which.

Referring to FIGS. 1 to 8, there is shown a monitoring apparatus 2 for monitoring a multiphase flow in a pipe using magnetic induction tomography.

Figure 1:
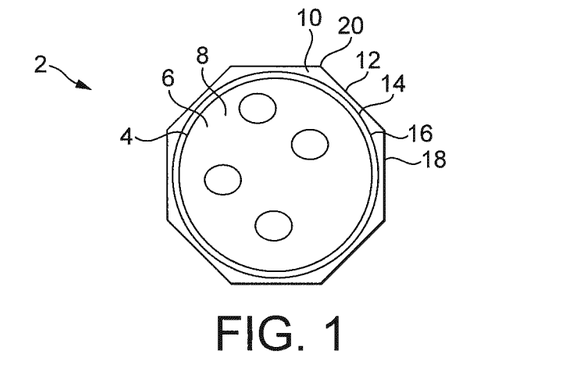
FIG. 1 is a schematic illustration of a cross-section through a tubular member of a monitoring apparatus for monitoring a multiphase flow through a pipe in accordance with an embodiment of the present invention.

The apparatus 2 comprises a pipe 4 defining a flow conduit 6. The pipe orientation can be horizontal, vertical, or any inclined position therebetween. In use, a multiphase flow 8 flows along the flow conduit 6 of the pipe 4. The multiphase flow 8 comprises at least two phases, optionally at least three phases, further optionally all of the phases, selected from an oil phase, an aqueous phase, a solid phase and a gaseous phase. In FIG. 1, two phase are shown schematically, comprising a continuous phase and a discontinuous phase. The multiphase flow 8 typically has a primary or continuous phase of the flow, e.g., oil, water or gas, and within the primary phase one or more other phase constituents may be present, for example a solid phase, e.g. sand. The flow regime of these phases can vary significantly depending on the concentrations of each phase and the flow rate.

The apparatus 2 further comprises a tubular member 10 adapted for fitting around the pipe 4. The tubular member 10 has outer and inner tubular surfaces 12, 14 surrounding a central longitudinal axis L-L of the tubular member 10. The inner tubular surface 14 defines a central bore 16 extending along the central longitudinal axis L-L for receiving the pipe 4 therealong. As described hereinafter, the tubular member 10 can be removably fitted around the pipe 4.

The portion of the pipe 4 surrounded by the tubular member 10 is preferably composed of a material, for example a non-metallic material such as a polymer, which permits electromagnetic field penetration, across a broad wavelength range, emitted from an energised electrical transmitter coil as described below, to pass through the multiphase material in the flow conduit 6 and then secondary induced electromagnetic radiation to be received by another electrical coil functioning as a receiver coil.

The outer tubular surface 12 has a polygonal cross-section and is comprised of a plurality of planar faces 18. Each planar face 18 extends parallel to the central longitudinal axis L-L. In the illustrated embodiment the outer tubular surface 12 is comprised of an annular array of planar faces 18. Typically, there is an even number of planar faces 18, the even number being within the range of from 4 to 12, for example 8. The planar faces 18 are preferably mutually adjacent, so that each longitudinal edge 20 of the planar face 18 is coincident with a longitudinal edge 20 of the planar face 18 on each side thereof. In the illustrated embodiment, the outer tubular surface 12 has an octagonal cross-section. The planar faces 18 are preferably each orthogonal to a respective radius of the tubular member 10.

The inner tubular surface 14 is preferably cylindrical. Typically the inner tubular surface 14 is shaped and dimensioned to fit tightly around a pipe 4, preferably a cylindrical pipe 4, of a given external diameter.

Figure 4:
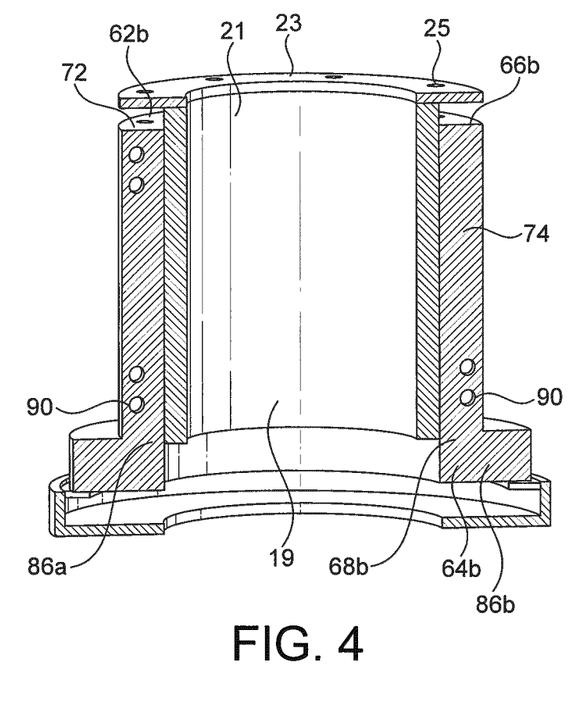
FIG. 4 is a schematic side view of a semi-cylindrical portion of one of the tubular members shown in FIG. 1, and sleeve removably disposed therein.
Figure 5:
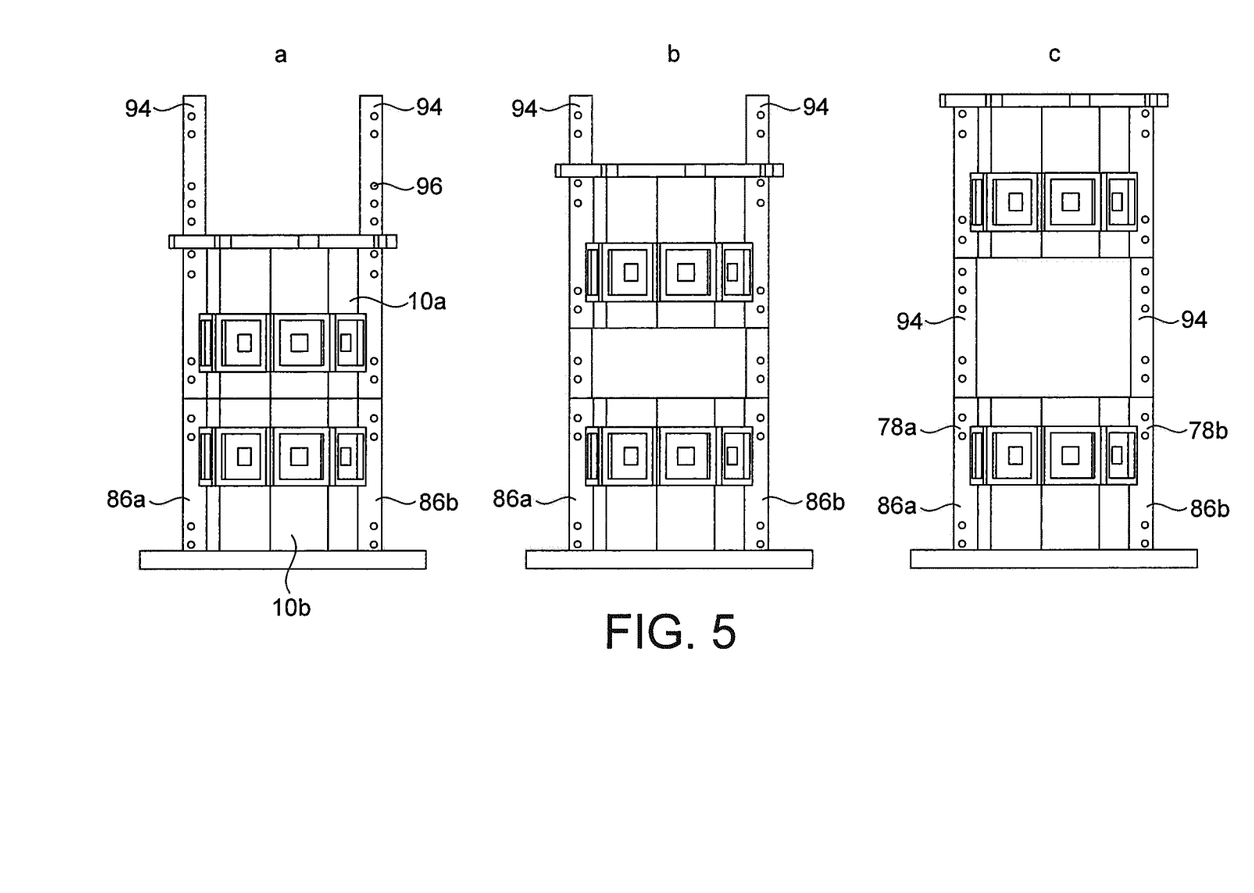
FIGS. 5a, 5b and 5c are schematic side views of the two tubular members as shown in Figure which are mounted to an elongate mounting element in three respective alternative configurations.

However, as shown in FIG. 4 an inner sleeve member 21 may be removably fitted within the inner tubular surface 14 to reduce the internal diameter of the central bore 16 which receives the pipe 4. The inner sleeve member 21 comprises a cylindrical portion 19 and an integral flange portion 23, the flange portion 23 having an array of holes 25 extending therethrough. Preferably, the inner sleeve member 21 is an assembly of two semi-cylindrical portions to form a cylindrical sleeve.

Figure 2:
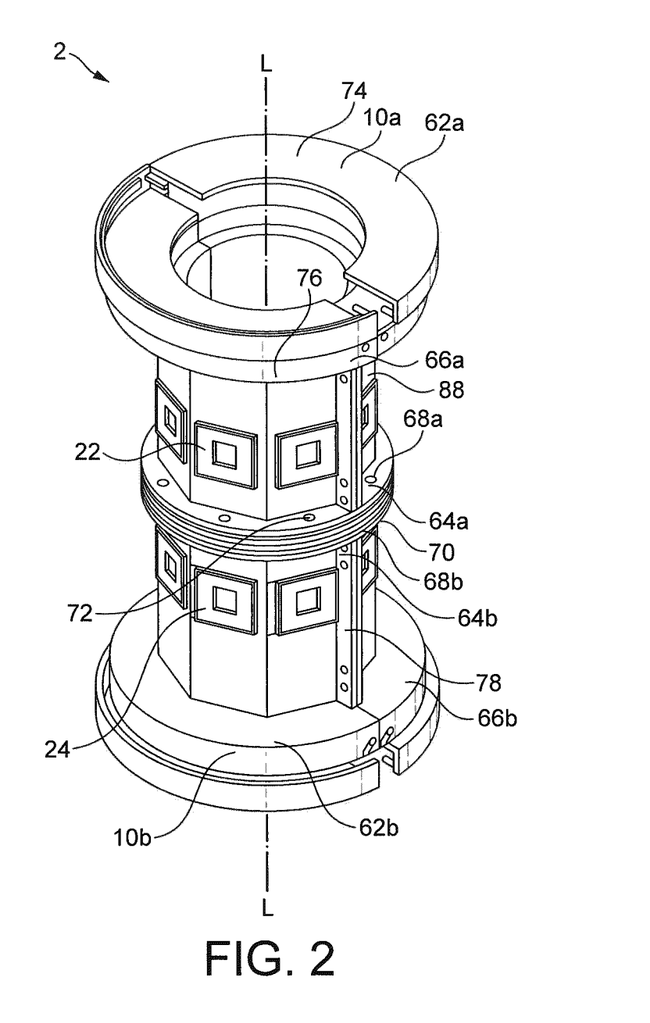
FIG. 2 is a schematic perspective view of a monitoring apparatus comprising two connected tubular members of the apparatus of FIG. 1.
Figure 3:
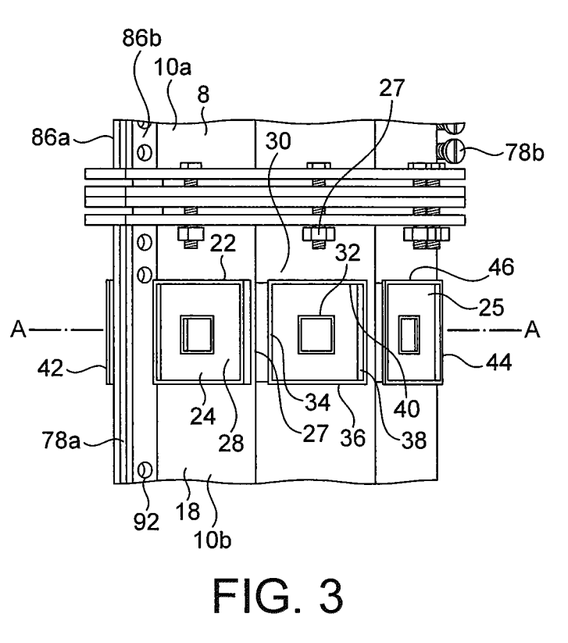
FIG. 3 is a schematic side view of a central part of the two connected tubular members shown in FIG. 2.
Figure 6:
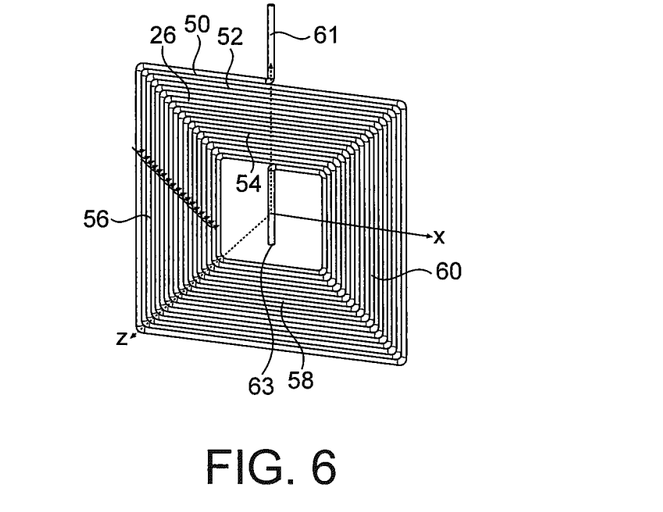
FIG. 6 is a schematic perspective view of an electrical transmitter/receiver coil for mounting in the monitoring apparatus of FIG. 1.

Referring in particular to FIGS. 2 and 3, at least two of the planar faces 18 each includes a respective coil mounting portion 22 configured for mounting a respective electrical coil thereon. In the illustrated embodiment, each of the planar faces 18 includes a respective coil mounting portion 22. The coil mounting portion comprises a recess 24 in the tubular outer surface 12 which is adapted to receive an electrical coil 26, which is shown in FIG. 6. The coil mounting portion 22 can function to receive a preformed electrical coil 26, or alternatively the coil mounting portion 22 can function as a coil former, which enables an electrical wire to be wound in situ into a coil within the coil mounting portion 22.

The recess 24 has a planar lower surface 28 and is polygonal in plan, for example rectangular in plan. However, the coil mounting portion 22 may have any desired shape in plan to accommodate any desired coil geometry; for example the coil mounting portion 22 may be circular in plan to accommodate a circular coil.

The recess 24 is typically defined between outer and inner peripheral edges 30, 32 which are raised above the respective planar face 18. In the illustrated embodiment, the recess 24 is composed of four linear sections 34, 36, 38, 40 and is square in plan.

Preferably, first and second coil mounting portions 22 are disposed on respective diametrically opposite first and second sides 42, 44 of the tubular member 10. Typically, a central axis A-A of the first coil mounting portion 22 is coaxial with a central axis A-A of the second coil mounting portion 22. However, in the illustrated embodiment there is a respective coil mounting portion 22 on each of the planar faces 18 of the outer tubular surface 12. The coil mounting portions 22 form a ring 46 of the coil mounting portions 22 around the tubular member 10. The central axes A-A of the coil mounting portions 22 of the ring 46 are in a common plane which is orthogonal to the longitudinal axis L-L.

Referring to FIG. 6, a coil 26 is mounted in each coil mounting portion 22. Each coil mounting portion 22 is configured for mounting a respective coil 26 thereon in an orientation such that the central axis Z of the coil 26 is aligned with a radius of the tubular member 4.

In accordance with the preferred embodiments of the present invention, the coils 26 have a polygonal structure which has unexpectedly been found to provide an enhanced analysis of the multiphase flow by magnetic induction tomography as compared to known coil designs utilized in the prior art as discussed hereinabove.

The coil 26 comprises an electrically conductive wire 50 which is wound about a central axis Z to form a plurality of wire turns 52. Each turn 52 is in a common plane XY so that the respective coil 26 is planar. Each turn 52 is composed of a plurality of linear sections 54, 56, 58, 60, and the respective coil 26 is polygonal in plan, for example square in plan in the illustrated embodiment. In the preferred embodiment, successive wire turns 52 are mutually adjacent and in contact, and more preferably in contact along the entire length of each turn 52. This provides that there is no gap between the adjacent wire turns 52 of the coil 26. Typically, the coil 26 has from 10 to 30 turns, optionally from 15 to 25 turns, for example 18 turns. Typically, the coil 26 has an external dimension, in the plane XY of the coil 26, within the range of from 20 to 50 mm, optionally from 25 to 45 mm.

The planar coil 26 is aligned with the respective planar face 18 including the respective coil mounting portion 22. The coil 26 is fitted into the correspondingly shaped recess 24. The ends 61, 63 of the coil 26 are connected to a driver of a controller for driving the coils 26 in a transmitting or receiving mode.

Instead of using a wire, the coils may comprise an electrically conductive track on a substrate of electrically insulating material. The electrically conductive track may be printed or etched on the substrate. The substrate may be flexible.

Each coil mounting portion 22 is provided with a respective coil fixing mechanism 25 for fixing an electrical coil 26 to the respective coil mounting portion. The coil fixing mechanism 25 preferably comprises a slidable plate 27 which is slidably attached to the coil mounting portion 22 and is arranged to sandwich the coil 26 between the slidable plate 27 and the respective planar face 18.

FIGS. 2 and 3 illustrate two tubular members 10a, 10b connected together. Each tubular member 10a, 10b comprises a respective ring 46 of the coil mounting portions 22. In the illustrated embodiment, each tubular member 10a, 10b comprises a pair of annular first and second flanges 62a, 62b, 64a, 64b. Each first and second flange 62a, 62b, 64a, 64b is affixed to, or integral with, a respective longitudinal end 66a, 66b, 68a, 68b of the respective tubular member 10a, 10b.

The second flange 64a, 64b of each tubular member 10a, 10b includes a respective ring 70 of fitting holes 72 for fitting together the respective second flanges 64a, 64b thereby serially to connect together, using bolts 27, the adjacent tubular members 10a, 10b in a direction extending along the central longitudinal axis L-L.

When the inner sleeve member 21 is removably fitted within the inner tubular surface 14 to reduce the internal diameter of the central bore 16 which receives the pipe 4, the flange portion 23 of each of the respective inner sleeve members 21, each inner sleeve member 21 being disposed within a respective tubular member 10a, 10b, is located between the second flanges 64a, 64b. The holes 25 in the flange portions 23 are aligned with the holes 72 in the second flanges 64a, 64b of the tubular members 10a, 10b.

As shown in FIGS. 2 to 4, the tubular member 10 preferably comprises a plurality of part-tubular portions 74, 76 and at least one attachment mechanism 78 for attaching together the plurality of part-tubular portions 74, 76 to form the tubular member 10. In the illustrated embodiment, the part-tubular portions 74, 76 comprise first and second semi-cylindrical portions 74, 76. As illustrated, the tubular member 10 comprises first and second attachment mechanisms 78a, 78b on opposite longitudinal sides 42, 44 of the tubular member 10.

Typically, the attachment mechanism 78 comprises a pair of longitudinal flange members 86a, 86b, each flange member 86a, 86b being affixed to, or integral with, a respective one of the part-tubular portions 74, 76. A fixing device 88 is provided for fixing together the pair of longitudinal flange members 86a, 86b. In the illustrated embodiment, the longitudinal flange members 86a, 86b include at least one fixing hole 90 extending therethrough and the fixing device 88 comprises at least one bolt mechanism 92 for passage through aligned fixing holes 90 of the longitudinal flange members 86a, 86b to attachment together the longitudinal flange members 86a, 86b.

Alternatively, the tubular member 10 may comprise an attachment mechanism 78 on one longitudinal side of the tubular member 10 and a hinge mechanism (not shown) on an opposite longitudinal side of the tubular member 10, the hinge mechanism hingedly connecting the first and second semi-cylindrical tubular portions 74, 76 by a hinge extending parallel to the central longitudinal axis L-L.

As shown in FIGS. 5a to 5c, in an alternative embodiment, wherein the attachment mechanism 78 further comprises at least one elongate mounting element 94 to which the pair of longitudinal flange members 86a, 86b are fitted by the fixing device 88. The elongate mounting element 94 is adapted to define a plurality of indexed mounting positions therealong, whereby the pair of longitudinal flange members 86a, 86b may be fitted to the elongate mounting element 94 at a desired indexed mounting position therealong. Typically, the plurality of indexed mounting positions is defined by a plurality of mounting holes 96 serially arranged along the elongate mounting element 94. FIGS. 5a to 5c show three alternative positions of two tubular members 10a, 10b mounted to opposite common elongate mounting element 94s by diametrically opposite attachment mechanisms 78a, 78b. Each position enables the two tubular members 10 to be mutually separated by a desired given distance in a direction along the central longitudinal axis L-L. The elongate mounting element 94 functions as a guide mechanism that ensures a precise distance between the planes of mutually spaced rings of coils.

Typically, the coil mounting portion 22 is composed of an electrically non-conductive material, for example a polymer. This enables electromagnetic radiation to be transmitted from the coil 26 into the fluid conduit 8, and for secondary electromagnetic radiation to be received by the coil 26 from the fluid conduit 8. The remainder of the tubular member 10 may be composed of an electrically conductive material, for example a metal such as aluminium, to provide shielding against extraneous electromagnetic radiation and to prevent or minimize interference of the transmission and reception of electromagnetic by the coils 26. Alternatively, the planar faces 18 of the tubular member 10, and optionally the entire tubular member 10, may be made of an electrically non-conductive material. These elements may be made by 3D printing.

One or more shielding elements may be mounted to or within the tubular member 10 to provide shielding against extraneous electromagnetic radiation and to prevent or minimize interference of the transmission and reception of electromagnetic by the coils 26.

Figure 7:
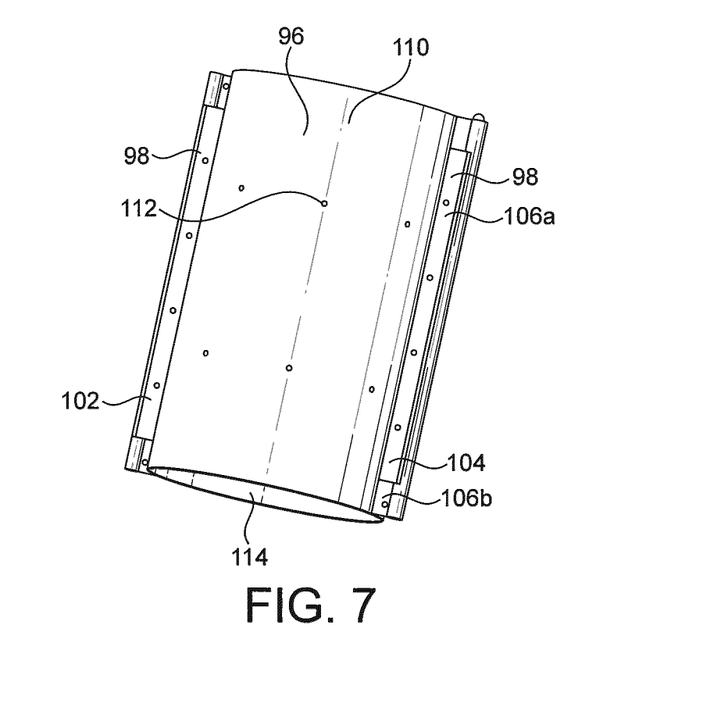
FIG. 7 is a schematic perspective view of a shield member for mounting on the monitoring apparatus of FIG. 1.

Referring to FIG. 7, the monitoring apparatus 2 further comprises a tubular shield member 96 adapted to be fitted around the tubular member 10. The shield member 96 is composed of an electrically conductive material to shield against electromagnetic radiation.

In one embodiment, the shield member 96 has at least one longitudinal flange 98 which is adapted to be clamped to a longitudinal edge of the tubular member 10. Alternatively, the shield member 96 may be clamped in a tubular configuration so as to have an internal diameter which corresponds to an external diameter of at least one part of the tubular member 10, for example one or more of the annular flanges 62a, 62b, 64a, 64b, thereby to compression fit the shield member 96 to the tubular member 10.

In the illustrated embodiment of FIG. 7, the shield member 96 has opposite first and second longitudinal edges 102, 104. At each of the opposite longitudinal edges 102, 104 of the shield member 96, a pair of overlapping flange portions 106a, 106b is provided which are adapted to be fitted together to close the shield member 96 in a tubular configuration. As shown in greater detail in FIG. 8, a gasket 108 composed of an electromagnetic interference (EMI) material may be disposed between the pair of overlapping flange portions 106a, 106b.

In an alternative embodiment, the shield member 96 may have a hinge 100 extending long the first longitudinal edge 102 of the shield member 96 and at the opposite second longitudinal edge 104 of the shield member 96, the pair of overlapping flange portions 106a, 106b is provided which are adapted to be fitted together to close the shield member 96 in a tubular configuration.

The shield member 96 is typically composed of a metallic material, such as aluminium, having a thickness greater than a minimum thickness of the particular shield material completely to absorb or reflect, and thereby fully shield, the electromagnetic radiation at the specified operating frequency of the driver system for driving the transmitter coils. The shield member 96 provides electrical continuity circumferentially around the coils and along a sufficient longitudinal length of the monitoring apparatus to ensure complete electromagnetic shielding of the transmitter/receiver coils. Typically, an aluminium shield member 96 has a thickness greater than 1 mm.

Figure 8:
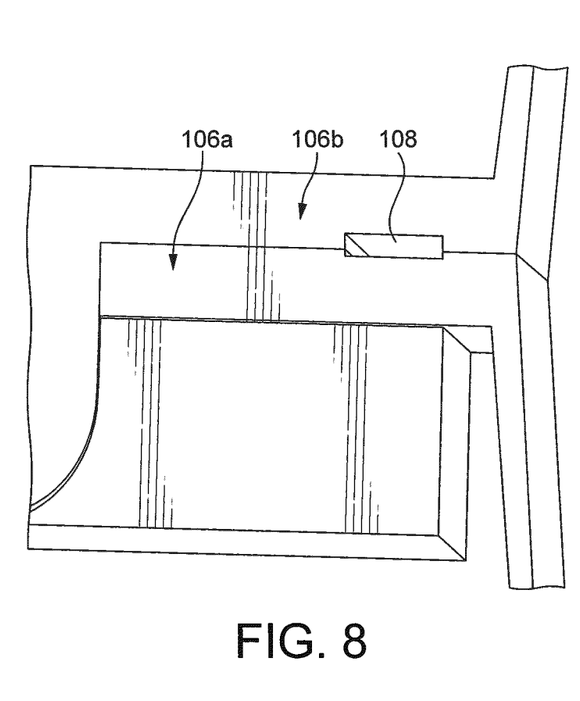
FIG. 8 is a detailed cross-section though overlapping flanges of the shield member of FIG. 7.

The overlapping flange construction in the shield member 96 ensures electrical conductivity across the overlapping portions 106a, 106b. The overlapping flange construction further permits the installation of an EMI gasket by means of which electromagnetic field leakage through the seam is avoided or minimised. The attachment mechanism of the shield member 96 allows installation around long pipes.

As also shown in FIG. 7, in the illustrated embodiment a cylindrical wall 110 of the shield member 96 is provided with at least one array of holes 112 extending therethrough for passage therethrough of wires connected to respective coils 26 mounted on respective coil mounting portions 22. Such an array of holes 112 enables wires to connect to the coils though individual independent holes of minimum dimensions in the shield member 96 which minimises transmission of electromagnetic radiation though the shielding member 96 and ensures maximum coil integrity.

The shield member 96 is supported in position around the tubular member 10 preferably by bolts that fit one longitudinal flange, or opposite longitudinal flanges, of the shield member 96 to corresponding longitudinal flanges of the tubular member 10.

The shield illustrated in FIG. 7 has open opposite longitudinal ends 114, and thereby forms an open-ended tube. However, in an alternative embodiment the shield of FIG. 7 may be modified to have closed longitudinal ends 114 and incorporates annular end plates which, in use, surround the pipe and enclose respective ends of the tubular member or tubular member assembly covered by the surrounding shield, thereby to form a closed-end tube. Therefore either an 'open' shield system without end plates or a "closed" shield system with end plates may be employed in any embodiment of the present invention.

The preferred embodiments of the present invention can provide that the coils are precisely positioned around the pipe, with the coils being equally spaced and axially symmetrical with respect to the cross section of the pipe. The monitoring apparatus can provide a precise distance between the planes of coils to ensure that measurements are repeatable.

The preferred embodiments of the present invention can provide a unitary single structure combining both coil mounts or formers and a clamp-on unit for securely fitting to a pipe. This arrangement ensures that the coils are fixed and so measurements are rigorous and repeatable. The combination between the material properties and fixing mechanism allows the unit to remain fixed around the pipe and withstand at least its own weight and the weight of the shield, which is configured to have a selected diameter and length sufficient to cover the tubular clamp-on mechanism.

By providing the combination of an inner cylindrical geometry and an outer polygonal geometry, for example an octagonal outer geometry to provide eight transmitter/receiver coils per plane, as shown in the illustrated embodiment, the outer polygonal cross-section can avoid deformation of the geometry of planar coils and the inner circular cross-section ensures accurate and reliable coupling with the external geometry of a pipe.

In use, one of the coils 26 of the array in the tubular member 10, 10b is configured to function as a transmitter coil, and one or more other coils of the array is configured to function as a receiver coil However, any of the coils may be adapted to transmit an electromagnetic field into the flow conduit 6 when energized by an input electrical signal and/or to receive an electromagnetic field from the flow conduit 6 and generate an output electrical signal, as described in detail hereinafter. In one embodiment one coil is always a transmitter and one or more other coils is or are always a receiver; in other embodiments the coils alternate between functioning as the transmitter and as the receiver. Fundamentally, any arrangement or control of the coils may be employed which can transmit an electromagnetic field into multiphase flow 8 in the flow conduit 6 and receive a resultant electromagnetic field from the multiphase flow 8 in the flow conduit 6, and thereby generate an output electrical signal to be used to analyse the phase composition of the multiphase flow 8 using magnetic induction tomography.

The coil are electrically connected to a controller which comprises a driver for providing alternating electrical current, i.e. AC current, at a selected frequency to the transmitter coil. Typically, the AC current has a frequency of from 1 kHz to 30 MHz, for example from 1 kHz to 10 MHz. The controller also comprises a data acquisition system coupled to a processor. The data acquisition system receives the induced electrical current from the receiver coil, and the current is analysed, by use of the processor, to provide an output signal which can provide, or be further analysed to provide, a phase measurement, of the multiphase flow, by magnetic induction tomography.

Thus a varying electric current is passed through the transmitter coil, which may have the properties of a sine wave, or another form, e.g. square wave, and all other potential forms of varying current are encompassed by the present invention. The varying electric current passing through the coil generates a varying electromagnetic flux through the multiphase flow 8 that is within the pipe 4. Depending on the physical properties of the different phases that the electromagnetic flux lines interrogate and in particular the electrical conductivity contrast between the phases, for example the oil and aqueous phases, a varying current is induced in the any electrically conductive phase. This induced current in turn generates a secondary varying electromagnetic field that propagates through the pipe 4 and is picked up by another coil that is used as a receiver. The secondary varying electromagnetic field therefore induces a varying current in the receiver coil. By comparing the driving and induced currents using appropriate processing, for example, the phase shift between the signals, allows the conductivity contrast between the materials of the multiphase flow to be computed.

In one embodiment, two coils can function in a fixed operating mode, i.e. a first coil acts as a transmitting coil and a second coil acts as a receiving coil, or in a dynamic operating mode, i.e. first and second coils can be switched so as to alternate between functioning as a transmitting coil and as a receiving coil.

In further embodiments, additional coils are provided, which preferably have the same planar and polygonal coil structure as described above. When more than two coils are provided, typically one coil may function as a transmitter and other coils may function as a receiver, so that, for example, at any point in time there is one coil that is transmitting and all of the other coils are receiving. Once all the receiver coil signals have been processed, one or more of the other coils becomes the transmitter and again the remainder are receivers and so forth.

It will be appreciated by those skilled in the art that the sequencing may take place in any order and that a complete cycle of measurements, that is, where every coil has been the transmitter once, can occur very rapidly with, e.g., 160 to 8000, for example 500 to 5000, measurement cycles every second. This frequency being primarily limited only by the processing power of the processor. It will also be appreciated by those skilled in the art that after one complete cycle of measurements a mesh of properties is produced that can be processed to provide a mesh or image of the multiple phases across the section of the pipe.

Although this description describes each coil being either a transmitter or receiver, clearly, a configuration can be provided whereby certain coils are always transmitters and others are always receivers. In other embodiments coils can be enclosed within other coils so that dedicated transmitter and receiver coils are at the same location. Those skilled in the art will appreciate that many combinations are possible and all such combinations may be are employed in this invention.

As described in the Applicant's prior patent specifications as summarised above, in alternative embodiments respective pairs of transmitting and receiving coils may be separated by a known fixed distance along the flow direction of the pipe. Each pair of transmitting and receiving coils may be operated as described above and can provide independent meshes or images of the flow at two points along the pipe.

It is possible to cross-correlate the measurements from two transmitter/receiver pairs, in order to establish the time-of-flight of features that represent different phases in the multiphase flow. The time difference between the features provides the time it takes for the phase to travel over the fixed distance. Those skilled in the art will appreciate that the velocity of this phase is readily computed from this information. Correspondingly, a velocity profile across the cross section of the pipe may be obtained. That is, a mesh or image of velocities can be produced that can be used to establish the velocity differences between the primary/continuous phase, and any other phase. Such velocities can be obtained when the primary or continuous phase is either conducting (e.g. water) or non-conducting fluid (e.g. oil).

The electromagnetic measurement as described above can provide phase measurements where there is a conductivity contrast between the phases. This is possible when the different phases or constituents are flowing in a predominately conducting (e.g. water) or non-conducting (e.g. oil) primary phase.

Furthermore, as shown in FIGS. 2 and 3, alternative embodiments of the monitoring apparatus of the present invention for monitoring a multiphase flow in a pipe using magnetic induction tomography may comprise a plurality of, for example two, annular arrays of the transmitter/receiver coils disposed around the pipe which defines therein an imaging space. In the first array, each coil of a first array is adapted to transmit an electromagnetic field when energized by an input electrical signal, and in the second array each coil is adapted to receive an electromagnetic field and generate an output electrical signal.

Preferably, the coils are circumferentially offset in a direction around the pipe 4, with respect to a respective adjacent coil, to reduce or minimise direct electromagnetic coupling between the respective coils.

In some preferred embodiments, the coils are each provided on a respective sheet of electrically insulating material, and the coil and the sheet of electrically insulating material comprises a flexible printed circuit board.

As described in the Applicant's prior patent specifications, the electrical current may be selectively switched through selected coils in an array to generate from each energized coil a local electromagnetic field. Typically, an impedance (not shown) connected to at least some of the respective selected coils in the array is provided to modify the magnitude of the local electromagnetic field generated from the respective energized coil element.

In one embodiment, the electrical current may be selectively switched through selected coils in the array to provide a composite electromagnetic field generated from the energized coils, when transmitting, and the energized coils have a controllable focal point within the pipe.

In another embodiment, the electrical current may be selectively switched through selected first coils in an array to provide a composite electromagnetic field received by second coils, when receiving, from a controllable focal point within the pipe. The controllable focal point may be scanned across the array of first and second coils to scan the generated electromagnetic field across a cross-section of the pipe and/or along a flow direction along the pipe. The scanning of the controllable focal point may be across a plurality of points to provide a pixelated image of the multiphase flow.

Various other embodiments of the monitoring apparatus and method of the present invention within the scope of the appended claims will readily be apparent to those skilled in the art.

The invention claimed is:

1. A monitoring apparatus for monitoring a multiphase flow in a pipe using magnetic induction tomography, the apparatus comprising a tubular member adapted for fitting around a pipe defining a flow conduit, wherein the tubular member has outer and inner tubular surfaces surrounding a central longitudinal axis of the tubular member, the inner tubular surface defining a central bore extending along the central longitudinal axis for receiving a pipe therealong, wherein the outer tubular surface has a polygonal cross-section and is comprised of an annular array of a plurality of planar faces, each planar face extending parallel to the central longitudinal axis, wherein at least two of the planar faces each includes a respective coil mounting portion on which is mounted a respective electrical coil, wherein the coil mounting portion comprises a recess in the tubular outer surface which receives a respective electrical coil, the monitoring apparatus further comprising at least one coil fixing mechanism for fixing the electrical coil to a respective coil mounting portion, wherein the coil fixing mechanism comprises a slidable plate which is slidably attached to the coil mounting portion and is arranged to sandwich the electrical coil between the slidable plate and the respective planar face.

2. A monitoring apparatus according to claim 1 wherein the at least two planar faces are each orthogonal to a respective radius of the tubular member.

3. A monitoring apparatus according to claim 1 wherein each coil mounting portion mounts a respective electrical coil thereon in an orientation such that a central axis of the electrical coil is aligned with a radius of the tubular member.

4. A monitoring apparatus according to claim 1 wherein the annular array of planar faces comprises an even number of planar faces, the even number being within the range of from 4 to 12, optionally 8, and each planar face includes a respective coil mounting portion on which a respective electrical coil is mounted in a respective recess.

5. A monitoring apparatus according to claim 1 wherein the inner tubular surface is cylindrical.

6. A monitoring apparatus according to claim 1 further comprising an inner sleeve member removably fitted within the inner tubular surface to reduce the internal diameter of the central bore.

7. A monitoring apparatus according to claim 1 wherein the tubular member comprises a plurality of part-tubular portions and at least one attachment mechanism for attaching together the plurality of part-tubular portions to form the tubular member.

8. A monitoring apparatus according to claim 7 wherein the tubular member comprises first and second semi-cylindrical portions and at least one attachment mechanism for attaching together the first and second semi-cylindrical portions to form the tubular member.

9. A monitoring apparatus according to claim 8 wherein the tubular member comprises first and second attachment mechanisms on opposite longitudinal sides of the tubular member or an attachment mechanism on one longitudinal side of the tubular member and a hinge mechanism on an opposite longitudinal side of the tubular member, the hinge mechanism hingedly connecting the first and second semi-cylindrical tubular portions by a hinge extending parallel to the central longitudinal axis.

10. A monitoring apparatus according to claim 7 wherein the attachment mechanism comprises a pair of longitudinal flange members, each flange member being affixed to, or integral with, a respective one of the part-tubular portions, and a fixing device for fixing together the pair of longitudinal flange members.

11. A monitoring apparatus according to claim 10 wherein the longitudinal flange members include at least one fixing hole extending therethrough and the fixing device comprises at least one bolt mechanism for passage through aligned fixing holes of the longitudinal flange members to attach together the longitudinal flange members.

12. A monitoring apparatus according to claim 10 wherein the attachment mechanism further comprises at least one elongate mounting element to which the pair of longitudinal flange members are fitted by the fixing device.

13. A monitoring apparatus according to claim 12 wherein the elongate mounting element is adapted to define a plurality of indexed mounting positions therealong, whereby the pair of longitudinal flange members may be fitted to the elongate mounting element at a desired indexed mounting position therealong.

14. A monitoring apparatus according to claim 13 wherein the plurality of indexed mounting positions is defined by a plurality of mounting holes serially arranged along the elongate mounting element.

15. A monitoring apparatus according to claim 1 wherein the tubular member further comprises a pair of annular flanges, each annular flange being affixed to, or integral with, a respective longitudinal end of the tubular member and wherein at least one annular flange of the pair of annular flanges includes a ring of fitting holes for fitting the respective annular flange to another corresponding annular flange including a respective ring of fitting holes thereby serially to connect together adjacent tubular members in a direction extending along the central longitudinal axis.

16. A monitoring apparatus according to claim 1 wherein the recess has a planar lower surface and is polygonal in plan.

17. A monitoring apparatus according to claim 1 wherein the recess is defined between outer and inner peripheral edges which are raised above the respective planar face.

18. A monitoring apparatus according to claim 1 wherein the recess is composed of four linear sections and is rectangular in plan, optionally square in plan.

19. A monitoring apparatus according to claim 1 wherein the electrical coil comprises an electrically conductive wire which is wound about a central axis to form a plurality of wire turns, wherein each turn is in a common plane so that the respective electrical coil is planar and each turn is composed of a plurality of linear sections and the respective electrical coil is polygonal in plan, and the planar electrical coil is aligned with the respective planar face including the respective coil mounting portion.

20. A monitoring apparatus according to claim 1 wherein the coil mounting portion of the respective planar face of the tubular member, or the tubular member, is composed of an electrically non-conductive material.

21. A monitoring apparatus according to claim 1 further comprising a tubular shield member adapted to be fitted around the tubular member, the shield member being composed of an electrically conductive material to shield against electromagnetic radiation, optionally wherein a wall of the shield member is provided with at least one array of holes extending therethrough for passage therethrough of wires connected to respective coils mounted on respective coil mounting portions.

22. A monitoring apparatus according to claim 21 wherein the shield member has at least one longitudinal flange which is adapted to be clamped to a longitudinal edge of the tubular member.

23. A monitoring apparatus according to claim 21 wherein the shield member has a hinge extending along a first longitudinal edge of the shield member and, at an opposite second longitudinal edge of the shield member, a pair of overlapping flange portions which are adapted to be fitted together to close the shield member in a tubular configuration, optionally wherein a gasket composed of an electromagnetic interference material is disposed between the pair of overlapping flange portions.

* * * * *